United States Patent
Kuad et al.

(10) Patent No.: US 9,365,507 B2
(45) Date of Patent: Jun. 14, 2016

(54) DIARYL SULFONE COMPOUND, AND MANUFACTURING METHOD FOR SAME

(75) Inventors: Paul Kuad, Mulhouse (FR); Hisaaki Kanda, Hyogo (JP); Takeshi Fujiwara, Hyogo (JP); Hiroyuki Shiraishi, Hyogo (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 0 days.

(21) Appl. No.: 13/583,730

(22) PCT Filed: Mar. 9, 2011

(86) PCT No.: PCT/JP2011/055453
§ 371 (c)(1),
(2), (4) Date: Sep. 10, 2012

(87) PCT Pub. No.: WO2011/114955
PCT Pub. Date: Sep. 22, 2011

(65) Prior Publication Data
US 2013/0005982 A1    Jan. 3, 2013

(30) Foreign Application Priority Data

Mar. 18, 2010 (JP) .................. 2010-062880
Mar. 19, 2010 (JP) .................. 2010-064031

(51) Int. Cl.
C07C 317/14    (2006.01)
C07C 323/65    (2006.01)

(52) U.S. Cl.
CPC .................. *C07C 323/65* (2013.01)

(58) Field of Classification Search
CPC .................................................. C07C 317/14
USPC ............................................... 568/34
See application file for complete search history.

(56) References Cited

U.S. PATENT DOCUMENTS

| | | | |
|---|---|---|---|
| 4,808,696 A | 2/1989 | Takekoshi | |
| 5,183,917 A | 2/1993 | Maruyama et al. | |
| 5,932,731 A | 8/1999 | Goda et al. | |
| 2003/0218154 A1 | 11/2003 | Sasaki | |
| 2008/0200582 A1 | 8/2008 | Craciun et al. | |
| 2009/0163683 A1 | 6/2009 | Kim et al. | |
| 2010/0076106 A1* | 3/2010 | Iwasa et al. | 522/44 |
| 2010/0109317 A1 | 5/2010 | Hoffmüller et al. | |

FOREIGN PATENT DOCUMENTS

| | | |
|---|---|---|
| CN | 101636276 A | 1/2010 |
| JP | 3-38564 A | 2/1991 |
| JP | 3-109368 A | 5/1991 |
| JP | H3-153664 | 7/1991 |
| JP | H5-117234 | 5/1993 |
| JP | 8143532 A | 6/1996 |
| JP | 8143533 | 6/1996 |
| JP | 9-3058 A | 1/1997 |
| JP | 940636 A | 2/1997 |
| JP | 2785876 B2 | 5/1998 |
| JP | 2003-176332 A | 6/2003 |
| JP | 2003292541 A | 10/2003 |
| JP | 2004-176006 A | 6/2004 |
| JP | 2007-304154 A1 | 11/2007 |
| JP | 2008-197239 A1 | 8/2008 |
| JP | 2009-102550 A1 | 5/2009 |
| JP | 2009-120832 A1 | 6/2009 |
| JP | 2009-149649 A | 7/2009 |
| JP | 2010-97195 A1 | 4/2010 |
| JP | 2010-135652 A | 6/2010 |
| SU | 499261 A1 | 7/1976 |
| SU | 802275 A1 | 2/1981 |
| SU | 1421736 A1 | 9/1988 |
| WO | 90/04587 | 5/1990 |
| WO | 2008/101806 A2 | 8/2008 |

OTHER PUBLICATIONS

"A comparison of the effect of p-amino phenyl sulfone compounds in vitro and in vivo on tubercle bacilli," Youmans et al., American Review of Tuberculosis, 1946, vol. 54, p. 295-298, Table 1, X-2.*

(Continued)

*Primary Examiner* — Scarlett Goon
*Assistant Examiner* — Sonya Wright
(74) *Attorney, Agent, or Firm* — Kratz, Quintos & Hanson, LLP

(57) ABSTRACT

The present invention provides a diaryl sulfone compound represented by Formula (1):

$$R^5-S-\underset{R^3\ R^4}{\overset{R^2\ R^1}{\bigcirc}}-\underset{\overset{\|}{O}}{\overset{\overset{O}{\|}}{S}}-\underset{R^{4'}\ R^{3'}}{\overset{R^{1'}\ R^{2'}}{\bigcirc}}-S-R^5$$

wherein $R^1$ to $R^4$ and $R^{1'}$ to $R^{4'}$ are the same or different, and each represents hydrogen, $C_{1-4}$ alkyl, or halogen, and $R^5$ represents $C_{2-6}$ alkenyl, $C_{1-4}$ alkyl, or aromatic heterocyclic group;

a method for producing the diaryl sulfone compound represented by Formula (1) by reacting a 4,4'-dihaloarylsulfone compound with thiol salt compound having an alkylene group; and a method for producing the diaryl sulfone compound represented by Formula (1) by reacting a 4,4'-dihaloarylsulfone compound with a thiol salt compound having a hydroxyl group, and subjecting the resulting compound to reaction with a halogenating agent, followed by a dehydrohalogenation reaction.

9 Claims, No Drawings

(56) References Cited

OTHER PUBLICATIONS

Youmans et al., "A Comparison of the Effect of P-Amino Phenyl Sulfone Compounds in Vitro and in Vivo on Tubercle Bacilli," American Review of Tuberculosis; vol. 54; 1946; p. 295-298.*

STN/CAS online results JP 2009067938, Liu et al. (2009).*

Yang Bo, et al., "High Performance Polymer Optical Material," Chem. Ind. Press, Edition 1 (2005), pp. 31-35.

Liu, Jin-gang, et al., "Synthesis and properties of sulfonyl-substituted polyimides with high refractive indices and high transparency," Journal of Functional Materials, vol. 39, Issue 3 (2008), pp. 460-464.

Chinese Office Action dated Jun. 28, 2013, in the corresponding Chinese patent application No. 201180014496.2, with English translation.

Suzuki, Yasuo, et al., "Synthesis of Highly Refractive and Transparent Polyimides Derived from 4,4'-[p-Sulfonylbis(phenylenesulfanyl)]diphthalic Anhydride and Various Sulfur-containing Aromatic Diamines," Polymer Journal, vol. 40, No. 5 (2008), pp. 414-420.

Supplementary European Search Report dated Aug. 6, 2013, in the corresponding European application No. 11 75 6143.

Supplementary European Search Report dated Aug. 6, 2013, in the corresponding European application No. 11 75 6144.

U.S. Appl. No. 13/583,725, filed Sep. 10, 2012, Kuad et al.

King, Frank D., "Bioisosteres, Conformational Restriction, and Prodrugs — Case History: An Example of a Conformational Restriction Approach," Med. Chem., Principle and Practice, Chapter 14 (1994), pp. 206-208.

Charmas, Wladyslaw, et al., "Thioether Glycidyl Resins. VII.* Products of Condensation of Bis(4-Mercaptophenyl) Sulfide and Bis(4-Mercaptophenyl) Sulfone with Epichlorohydrin," Journal of Applied Polymer Science, vol. 39 (1990), pp. 1623-1633.

English Translation of the Office Action Issued in the Corresponding JP Patent Application No. 2011-050045, on Jan. 6, 2015.

G. Youmans, et al.; "A Comparison of the Effect of P-Amino Phenyl Sulfone Compounds In Vitro and In Vivo on Tubercle Bacilli;" American Review of Tuberculosis; vol. 54; 1946; pp. 295-298 (4 Sheets)/International Search Report.

International Search Report for International Application No. PCT/JP2011/055453 dated Apr. 19, 2011.

* cited by examiner

DIARYL SULFONE COMPOUND, AND MANUFACTURING METHOD FOR SAME

TECHNICAL FIELD

The present invention relates to a novel diaryl sulfone compound useful as a monomer for producing resin for organic optical materials or as an additive for organic optical resin; and to a method for producing the same.

BACKGROUND ART

Because optical materials formed from synthetic resin are light compared to inorganic materials such as glasses, excellent in molding processability and the like, and easy to handle, such optical materials have been widely used in various applications in recent years. Polystyrene resin, polymethylmethacrylate resin, polycarbonate resin, diethylene glycol diallyl carbonate resin, and the like have been heretofore used as such resin for organic optical materials.

When these resins for organic optical materials are used as, for example, plastic lenses for glasses, the resins must have a high refractive index to reduce the lens thickness. Further, an attempt has been made to use these resins as light-transmission bodies by providing a refractive index distribution to transparent resin.

However, previous resins for organic optical materials are not always satisfactory because these resins have drawbacks such as a low refractive index, a high birefringence, a high dispersibility, and the like; and are also poor in heat resistance and shock resistance. In particular, diethylene glycol diallyl carbonate resin (CR-39) and the like used as lens materials have a low refractive index (1.50). Therefore, when these resins are used as lenses, the edge thickness and the central thickness become thick, causing drawbacks such as degradation in the appearance of the lenses and an increase in the weight.

Consequently, attempts have been made to improve the refractive index of resin for organic optical materials. For example, as a monomer for producing resin having a high refractive index and excellent transparency, Patent Literature 1 and Patent Literature 2 listed below disclose a diaryl sulfide compound represented by the following chemical formula (a):

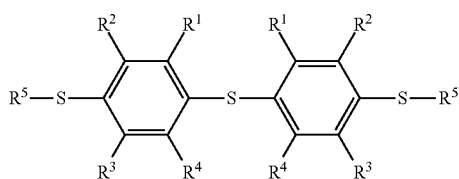

wherein $R^1$ to $R^4$ represent hydrogen, $C_{1-4}$ alkyl, or halogen, and $R^5$ represents $C_{2-6}$ alkenyl.

While these diaryl sulfide compounds are described as monomers for producing resin having a high refractive index and excellent transparency, the production of these compounds requires a 4,4'-dihalodiaryl sulfide compound, which is an expensive compound represented by the following chemical formula:

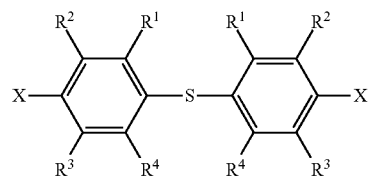

wherein $R^1$ to $R^4$ represents hydrogen, $C_{1-4}$ alkyl, or halogen, and X represents halogen. Accordingly, the diaryl sulfide compound of the above chemical formula (a) obtained using the 4,4'-dihalodiaryl sulfide compound as a starting material is costly, and the economic efficiency thereof is low. Therefore, there is a demand for a less-expensive material as a monomer that can be used for producing resin having a high refractive index and excellent transparency.

Meanwhile, diphenyl sulfone, diphenyl sulfone derivatives such as 4,4'-dichlorodiphenyl sulfone and 3,3'-4,4'-tetrachlorodiphenyl sulfone, and sulfur-containing compounds such as diphenyl sulfide and diphenyl sulfoxide are known as additives used for changing the refractive index of resin for organic optical materials (see Patent Literature 3 and Patent Literature 4 listed below).

However, of the above-described additives, diphenyl sulfone, diphenyl sulfone derivatives, and the like have a low refractive index (about 1.6), and these additives must be added in a large amount in order to increase the refractive index of the resin. This may deteriorate the properties of the resin, and it is not economically desirable.

Diphenyl sulfide, diphenyl sulfoxide, and the like require an expensive substance as a starting material for synthesis. Therefore, these compounds are costly, and are not economically desirable, particularly when they are added in a large amount.

CITATION LIST

Patent Literature

PLT 1: USSR Patent No. 499261
PLT 2: Japanese Patent No. 2785876
PLT 3: Japanese Unexamined Patent Publication No. 2007-304154
PLT 4: Japanese Unexamined Patent Publication No. 2008-197239

SUMMARY OF INVENTION

Technical Problem

The present invention was made in view of the current situation of the above-described conventional techniques. A main object of the present invention is to provide a novel compound that is useful as a monomer for producing synthetic resin having a high refractive index and excellent transparency, or as an additive for providing a high refractive index to resin for organic optical materials; that can be easily produced using an inexpensive starting material, under economically advantageous conditions; and that has performance at least equivalent to that of conventional compounds. The present invention also aims to provide a method for producing such a novel compound.

Solution to Problem

The present inventors conducted extensive studies to achieve the above-described objects, and as a result, found a novel diaryl sulfone compound that can be easily produced using a dihaloarylsulfone compound that is a relatively inexpensive substance as a starting material, under economically advantageous conditions. The present inventors found that, of such diaryl sulfone compounds, a diaryl sulfone compound having a specific substituent has an excellent performance as a monomer that can be used for producing resin having a high refractive index, a high hardness, and good transparency. The present inventors also found that, of such diaryl sulfone compounds, a diaryl sulfone compound having another specific substituent has a high refractive index (1.64 or higher), and is useful as an additive for providing a high refractive index to organic optical materials. The present invention was completed as a result of further studies based on these findings.

Specifically, the present invention provides the following novel diaryl sulfone compounds and method for producing the same.

Item 1. A diaryl sulfone compound represented by Formula (1):

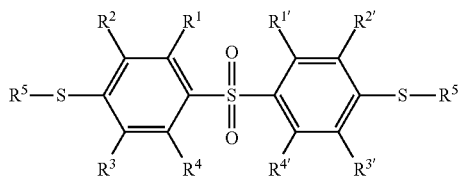

wherein $R^1$ to $R^4$ and $R^{1'}$ to $R^{4'}$ are the same or different, and each represents hydrogen, $C_{1-4}$ alkyl, or halogen; and $R^5$ represents $C_{2-6}$ alkenyl, alkyl, or aromatic heterocyclic group.

Item 2. The diaryl sulfone compound according to Item 1, wherein the aromatic heterocyclic group is an aromatic heterocyclic group having two or more different heteroatoms.

Item 3. The diaryl sulfone compound according to Item 1, wherein $R^5$ is vinyl, allyl, methyl, benzothiazolyl, or benzisothiazolyl.

tem 4. The diaryl sulfone compound according to Item 1, wherein $R^1$ to $R^4$ and $R^{1'}$ to $R^{4'}$ are all hydrogen; and $R^5$ is vinyl, allyl, methyl, benzothiazolyl, or benzisothiazolyl.

Item 5. A method for producing a diaryl sulfone compound represented by Formula (1-1):

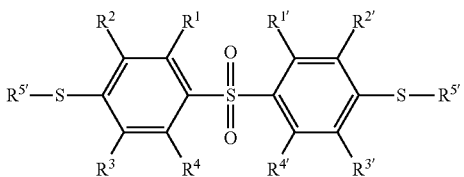

herein $R^1$ to $R^4$ and $R^{1'}$ to $R^{4'}$ are the same or different, and each represents hydrogen, $C_{1-4}$ alkyl, or halogen; and $R^{5'}$ represents $C_{3-6}$ alkenyl, $C_{1-4}$ alkyl, or aromatic heterocyclic group; the method comprising reacting a 4,4'-dihaloarylsulfone compound represented by Formula (2):

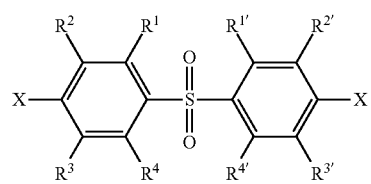

wherein $R^1$ to $R^4$ and $R^{1'}$ to $R^{4'}$ are as defined above, and X represents halogen;

with a thiol salt compound represented by Formula (3): $MSR^{5'}$ wherein M represents alkali metal, and $R^{5'}$ is as defined above.

Item 6. The method according to Item 5, wherein in the 4,4'-dihaloarylsulfone compound represented by Formula (2), $R^1$ to $R^4$ and $R^{1'}$ to $R^{4'}$ are all hydrogen, and X is chlorine.

Item 7. The method according to Item 5 or 6, wherein the thiol salt compound represented by Formula (3) is at least one compound selected from the group consisting of sodium-2-propenethiolate, potassium-3-butenethiolate, sodium methanethiolate, potassium-1-propanethiolate, sodium-2-propanethiolate, lithium-sec-butylthiolate, sodium-tert-butylthiolate, sodium-2-benzothiazolylthiolate, potassium-2-thiazolylthiolate, and sodium-3-isothiazolylthiolate.

Item 8. A method for producing a diaryl sulfone compound represented by Formula (1-2):

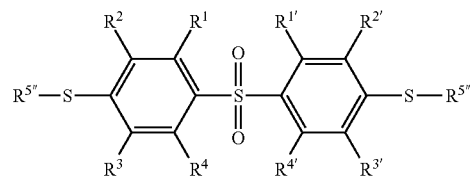

wherein $R^1$ to $R^4$ and $R^{1'}$ to $R^{4'}$ are the same or different, and each represents hydrogen, $C_{1-4}$ alkyl, or halogen; and $R^{5''}$ represents $C_{2-6}$ alkenyl;

the method comprising reacting a 4,4'-dihaloarylsulfone compound represented by Formula (2):

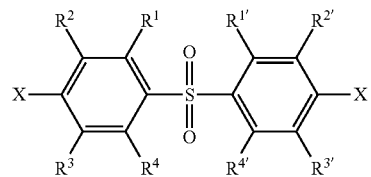

wherein $R^1$ to $R^4$ and $R^{1'}$ to $R^{4'}$ are as described above, and X represents halogen;

with a thiol salt compound represented by Formula (4): $MSR^6OH$, wherein M represents an alkali metal and $R^6$ represents $C_{2-6}$ alkylene; thereby producing a compound represented by Formula (5):

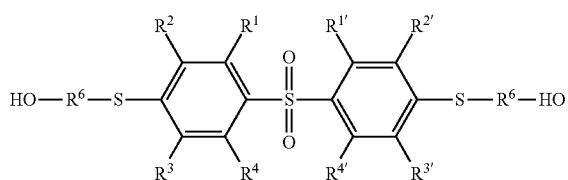

wherein $R^1$ to $R^4$, $R^{1'}$ to $R^{4'}$, and $R^6$ are as defined above; and subsequently reacting the resulting compound with a halogenating agent, thereby producing a compound represented by Formula (6):

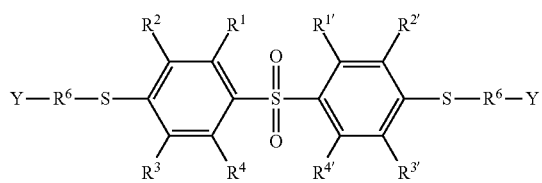

wherein $R^1$ to $R^4$, $R^{1'}$ to $R^{4'}$, and $R^6$ are as defined above, and Y represents halogen;
and subsequently reacting the resulting compound with a base to perform a dehydrohalogenation reaction.

Item 9. The method for producing a diaryl sulfone compound according to Item 8, wherein the thiol salt compound represented by Formula (4): $MSR^6OH$ is potassium-2-hydroxyethanethiolate or potassium-4-hydroxy-n-butylthiolate.

Item 10. The method for producing a diaryl sulfone compound according to Item 8 or 9, wherein the halogenating agent is at least one member selected from the group consisting of chlorine, thionyl chloride, hypochlorous acid, hypobromous acid, and bromine.

Item 11. The method for producing a diaryl sulfone compound according to any one of Items 8 to 10, wherein the base used in the dehydrohalogenation reaction of the compound represented by Formula (6) is at least one member selected from the group consisting of sodium hydroxide, potassium hydroxide, calcium hydroxide, lithium hydroxide, sodium carbonate, potassium carbonate, calcium carbonate, and lithium carbonate.

The novel diaryl sulfone compounds of the present invention and the method for producing the same are specifically described below.

Novel Diaryl Sulfone Compound

The diaryl sulfone compounds of the present invention are novel compounds not disclosed in any literature, and are represented by the following Formula (1):

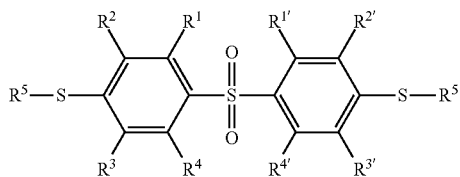

wherein $R^1$ to $R^4$ and $R^{1'}$ to $R^{4'}$ are the same or different, and each represents hydrogen, $C_{1-4}$ alkyl, or halogen; and $R^5$ represents $C_{2-6}$ alkenyl, $C_{1-4}$ alkyl, or aromatic heterocyclic group.

Of the diaryl sulfone compounds represented by Formula (1), a compound in which $R^5$ is $C_{2-6}$ alkenyl is a compound useful, for example, as a monomer that is used for producing synthetic resin for optical materials having a high refractive index and good transparency.

Further, of the diaryl sulfone compounds represented by Formula (1), a compound in which $R^5$ is $C_{1-4}$ alkyl or aromatic heterocyclic group is a substance having a high refractive index (1.64 or higher). When the compound is used, for example, as an additive to resin for organic optical materials, it can impart a high refractive index to the resin, even if the amount added is relatively small. Accordingly, adding the compound to resin for optical materials allows the production of optical materials having a high refractive index, without significantly affecting physical properties or the like.

In the above Formula (1), examples of $C_{1-4}$ alkyl represented by $R^1$ to $R^4$ and $R^{1'}$ to $R^{4'}$ include linear or branched alkyl groups such as methyl, ethyl, n-propyl, isopropyl, n-butyl, sec-butyl, and tert-butyl, with methyl being particularly preferable. Examples of halogen include chlorine, bromine, iodine, and the like, with chlorine being particularly preferable.

Of the groups represented by $R^5$, $C_{2-5}$ alkenyl is preferably linear or branched $C_{2-5}$ alkenyl having one or two carbon-carbon double bonds, and specific examples thereof include vinyl, allyl, isopropenyl, 1-butenyl, 2-butenyl, 3-butenyl, isobutenyl, and the like, with vinyl and allyl being particularly preferable.

Further, of the groups represented by $R^5$, specific examples of $C_{1-4}$ alkyl are the same as those alkyls represented by $R^1$ to $R^4$ and $R^{1'}$ to $R^{4'}$, with methyl being particularly preferable.

The aromatic heterocyclic group represented by $R^5$ may be an aromatic heterocyclic group containing at least one heteroatom selected from nitrogen, oxygen, and sulfur, in addition to carbon. Examples thereof include a 5- to 7-membered monocyclic heterocyclic group, a condensed heterocyclic group in which a 3- to 8-membered ring is condensed to the above-described monocyclic heterocyclic group, and the like. Specific examples of aromatic heterocyclic groups include thienyl, pyrrolyl, furyl, thiazolyl, isothiazolyl, imidazolyl, pyrazolyl, oxazolyl, pyridyl, pyrazinyl, pyrimidinyl, pyridazinyl, isooxazolyl, isoquinolyl, isoindolyl, indazolyl, indolyl, quinoxalinyl, quinolyl, benzothiazolyl, benzisothiazolyl, benzimidazolyl, benzofuranyl, and the like.

An aromatic heterocyclic group having two or more different heteroatoms is particularly preferable as the aromatic heterocyclic group. Specific examples thereof include monocyclic aromatic heterocyclic groups containing nitrogen and sulfur, such as thiazolyl, isothiazolyl and imidazolyl; and condensed aromatic heterocyclic groups containing nitrogen and sulfur, such as benzothiazolyl, benzisothiazolyl, and benzimidazolyl. In the present invention, benzothiazolyl, benzisothiazolyl, and the like are particularly preferable.

Specific preferable examples of the compounds represented by the above Formula (1) include a compound in which $R^1$ to $R^4$ and $R^{1'}$ to $R^{4'}$ are all hydrogen, and $R^5$ is vinyl; a compound in which $R^1$ to $R^4$ and $R^{1'}$ to $R^{4'}$ are all hydrogen, and $R^5$ is allyl; a compound in which $R^1$ to $R^4$ and $R^{1'}$ to $R^{4'}$ are all hydrogen, and $R^5$ is methyl; a compound in which $R^1$ to $R^4$ and $R^{1'}$ to $R^{4'}$ are all hydrogen, and $R^5$ is benzothiazolyl; and the like.

Specific examples of the compounds represented by Formula (1) include 4,4'-di(vinylthio)diphenyl sulfone, 4,4'-di(allylthio)diphenyl sulfone, 4,4'-di(isopropenylthio)diphenyl sulfone, 4,4'-di(3-butenylthio)diphenyl sulfone, 4,4'-di(methylthio)diphenyl sulfone, 4,4'-di(ethylthio)diphenyl sulfone, 4,4'-di(n-propylthio)diphenyl sulfone, 4,4'-di(2-benzothiazolylthio)diphenyl sulfone, 4,4'-di(2-thiazolylthio)diphenyl sulfone, 4,4'-di(3-isothiazolylthio)diphenyl sulfone, and the like.

Method for Producing Diaryl Sulfone Compound

A method for producing the diaryl sulfone compounds represented by the above Formula (1) is described below.

(1) First Method

In Formula (1), a diaryl sulfone compound in which $R^5$ is $C_{3-6}$ alkenyl, $C_{1-4}$ alkyl, or aromatic heterocyclic group, i.e., a diaryl sulfone compound represented by Formula (1-1):

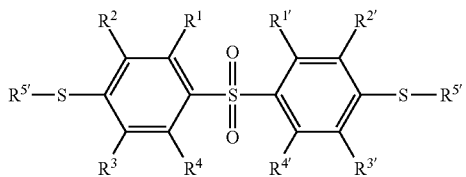

wherein $R^1$ to $R^4$ and $R^{1'}$ to $R^{4'}$ are the same or different, and each represents hydrogen, $C_{1-4}$ alkyl, or halogen; and $R^{5'}$ represents $C_{3-6}$ alkenyl, $C_{1-4}$ alkyl, or aromatic heterocyclic group; can be produced by reacting a 4,4'-dihaloarylsulfone compound represented by the following Formula (2):

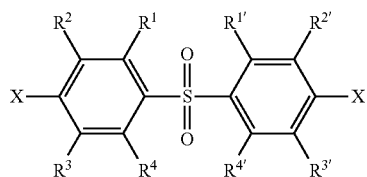

wherein $R^1$ to $R^4$ and $R^{1'}$ to $R^{4'}$ are the same or different, and each represents hydrogen, $C_{1-4}$ alkyl, or halogen; and X represents halogen;
with a thiol salt compound represented by Formula (3): $MSR^{5'}$, wherein M represents an alkali metal; and $R^{5'}$ represents $C_{3-6}$ alkenyl, $C_{1-4}$ alkyl, or aromatic heterocyclic group.

The 4,4'-dihaloarylsulfone compound of Formula (2) used as a starting material is a known compound and is a relatively less-expensive substance. In Formula (2), examples of the halogen represented by X include chlorine, bromine, iodine, and the like, with chlorine being particularly preferable.

In the thiol salt compound of the above Formula (3), examples of the alkali metal represented by M include sodium, potassium, lithium, and the like.

Examples of $C_{3-6}$ alkenyl represented by $R^{5'}$ include allyl, isopropenyl, 1-butenyl, 2-butenyl, 3-butenyl, isobutenyl, and the like.

The $C_{1-4}$ alkyl and aromatic heterocyclic groups represented by $R^{5'}$ are the same as those represented by $R^5$ in the above Formula (1).

Specific examples of the thiol salt compound of Formula (3) include sodium-2-propenethiolate, potassium-3-butenethiolate, lithium-2-butenethiolate, sodium methanethiolate, potassium-1-propanethiolate, sodium-2-propanethiolate, lithium-sec-butylthiolate, sodium-tert-butylthiolate, sodium-2-benzothiazolylthiolate, potassium-2-thiazolylthiolate, sodium-3-isothiazolylthiolate, and the like. Sodium-2-propenethiolate, sodium methanethiolate, sodium-2-benzothiazolylthiolate, and the like are preferable from an economic viewpoint.

The thiol salt compound of Formula (3) may be directly added as an alkali metal salt to the reaction solvent; or thiol represented by Formula: $HSR^{5'}$ and an alkali metal hydride (MH) or an alkali metal hydroxide (MOH) may be added to the solvent so as to form a salt in the solvent.

The amount of the thiol salt compound of Formula (3) used is preferably about 2 to 6 mol, more preferably about 2 to 3 mol, per mole of the 4,4'-dihaloarylsulfone compound of Formula (2).

Preferably, the reaction of the 4,4'-dihaloarylsulfone compound represented by Formula (2) with the thiol salt compound represented by Formula (3) is performed in a polar solvent such as dimethylsulfoxide, N-methylpyrrolidone, or N,N-dimethylformamide, or in a biphasic solvent of water and an organic solvent such as a halogenated hydrocarbon (e.g., methylene chloride, 1,2-dichloroethane, chlorobenzene, or o-dichlorobenzene) or a hydrocarbon (e.g., n-hexane, n-heptane, cyclohexane, toluene, xylene, or the like). From an economic viewpoint, use of N-methylpyrrolidone alone or a biphasic solvent of toluene and water is particularly preferable.

When a polar solvent is used, the reaction solvent is preferably used in an amount of about 10 to 5,000 parts by weight, more preferably about 100 to 1,000 parts by weight, relative to 100 parts by weight of the 4,4'-dihaloarylsulfone compound represented by Formula (2).

When a biphasic solvent is used, both organic solvent and water are preferably used in an amount of about 10 to 5,000 parts by weight, more preferably about 100 to 1,000 parts by weight, relative to 100 parts by weight of the 4,4'-dihaloarylsulfone compound represented by Formula (2).

When the reaction is carried out in a biphasic solvent, it is preferable to use a phase-transfer catalyst.

Examples of phase-transfer catalysts that can be used include quaternary ammonium salts such as benzyltriethylammonium bromide, benzyltrimethylammonium bromide, dodecyltrimethylammonium chloride, tetra-n-butylammonium bromide, tetraethylammonium bromide, and trioctylmethylammonium bromide; quaternary phosphonium salts such as hexadodecyltriethylphosphonium bromide, hexadodecyltributylphosphonium chloride, and tetra-n-butylphosphonium chloride; and the like. Tetra-n-butylammonium bromide is particularly preferable in view of the increased yield and the economic efficiency.

The amount of phase-transfer catalyst used is preferably about 0.1 to 100 parts by weight, more preferably about 0.1 to 10 parts by weight, relative to 100 parts by weight of the 4,4'-dihaloarylsulfone compound of Formula (2).

The reaction temperature is preferably about 30 to 150° C., and more preferably about 50 to 150° C. Particularly when producing a compound in which $R^5$ is $C_{2-6}$ alkenyl, the reaction temperature is preferably about 30 to 120° C., and more preferably about 50 to 110° C. within the above temperature ranges. When producing a compound in which $R^5$ is $C_{1-4}$ alkyl or aromatic heterocyclic group, the reaction temperature is preferably about 30 to 150° C., and more preferably about 60 to 150° C.

The reaction time is usually about 1 to 30 hours.

The specific reaction method is not particularly limited. Usually, a catalyst is added, if necessary, to the above-described solvent, and the 4,4'-dihaloarylsulfone compound represented by Formula (2) and the thiol salt compound represented by Formula (3) are uniformly mixed in the solvent. The order of addition of each component is not particularly limited, and any method can be employed.

The desired diaryl sulfone compound represented by Formula (1-1):

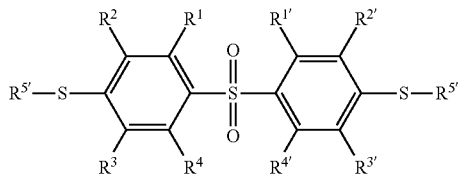

wherein $R^1$ to $R^4$ and $R^{1'}$ to $R^{4'}$ are the same or different, and each represents hydrogen, $C_{1-4}$ alkyl, or halogen; and $R^{5'}$ represents $C_{3-6}$ alkenyl, $C_{1-4}$ alkyl, or aromatic heterocyclic group; can be produced by the above-described method.

The resulting diaryl sulfone compound can be obtained, if necessary, by water-washing and liquid-liquid separation. The diaryl sulfone compound can also be isolated with high purity by recrystallization after distilling off the solvent.

Specific examples of the diaryl sulfone compound obtained by the above method include 4,4'-di(allylthio)diphenyl sulfone, 4,4'-di(3-butenylthio)diphenyl sulfone, 4,4'-di(isopropenylthio)diphenyl sulfone, 4,4'-di(methylthio)diphenyl sulfone, 4,4'-di(ethylthio)diphenyl sulfone, 4,4'-di(n-propylthio)diphenyl sulfone, 4,4'-di(2-benzothiazolylthio)diphenyl sulfone, 4,4'-di(2-thiazolylthio)diphenyl sulfone, 4,4'-di(3-isothiazolylthio)diphenyl sulfone, and the like.

(2) Second Method

Of the diaryl sulfone compounds represented by the above Formula (1), a diaryl sulfone compound in which $R^5$ is $C_{2-6}$ alkenyl; i.e., a diaryl sulfone compound represented by Formula (1-2):

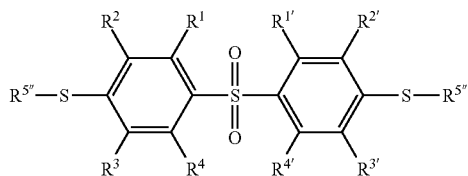

wherein $R^1$ to $R^4$ and $R^{1'}$ to $R^{4'}$ are the same or different, and each represents hydrogen, $C_{1-4}$ alkyl, or halogen; and $R^{5'''}$ represents $C_{2-6}$ alkenyl;

is also produced by another method. For example, there is a method in which a 4,4'-dihaloarylsulfone compound represented by the above Formula (2):

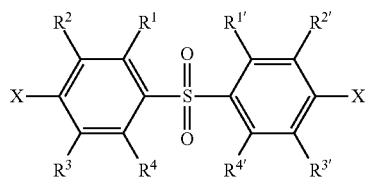

wherein $R^1$ to $R^4$ and $R^{1'}$ to $R^{4'}$, and X are as defined above; is reacted with a thiol salt compound represented by Formula (4): MSR$^6$OH, wherein M represents an alkali metal; and $R^6$ represents $C_{2-6}$ alkylene so as to produce a compound represented by Formula (5):

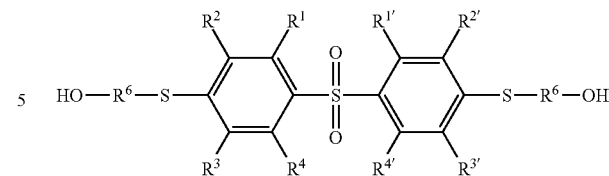

wherein $R^1$ to $R^4$, $R^{1'}$ to $R^{4'}$, and $R^6$ are as defined above;

subsequently, the resulting compound is reacted with a halogenating agent so as to produce a compound represented by Formula (6):

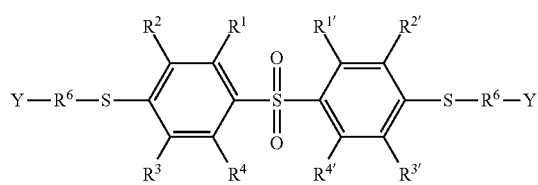

wherein $R^1$ to $R^4$, $R^{1'}$ to $R^{4'}$, and $R^6$ are as defined above; and Y is halogen;

then, the resulting compound is reacted with a base to perform a dehydrohalogenation reaction (HY elimination reaction), thereby producing a desired diaryl sulfone compound represented by Formula (1-2):

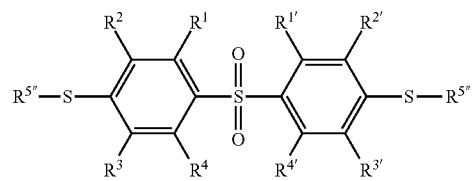

wherein $R^1$ to $R^4$ and $R^{1'}$ to $R^{4'}$ are the same or different, and each represents hydrogen, $C_{1-4}$ alkyl, or halogen; and $R^{5'''}$ represents $C_{2-6}$ alkenyl.

In the thiol salt compound represented by Formula (4): MSR$^6$OH, examples of the alkali metal represented by M include sodium, potassium, lithium, and the like. Examples of $C_{2-6}$ alkylene represented by $R^6$ include linear alkylene such as ethylene, trimethylene, tetraethylene, pentaethylene, and hexaethylene; and branched alkylene such as ethylethylene and 1,2-propylene.

The reaction of the 4,4'-dihaloarylsulfone compound represented by Formula (2) with the thiol salt compound represented by Formula (4) can be carried out under similar conditions as in the reaction of the 4,4'-dihaloarylsulfone compound represented by Formula (2) with the thiol salt compound represented by Formula (3) in the above-described first method. Similar to the thiol salt compound of Formula (3), the thiol salt compound represented by Formula (4) is also preferably used in an amount of about 2 to 6 mol, more preferably 2 to 3 mol, per mole of the 4,4'-dihaloarylsulfone compound of Formula (2).

The thiol salt compound of Formula (4) may be directly added as an alkali metal salt to the reaction solvent; or thiol represented by Formula: HSR$^6$OH and an alkali metal hydride (MH) may be added to the solvent so as to form a salt in the solvent.

The diaryl sulfone compound represented by Formula (5):

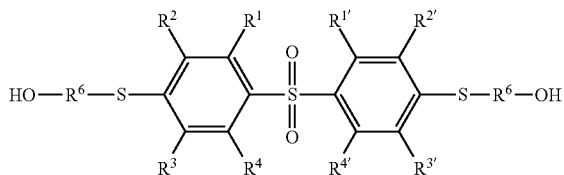

wherein $R^1$ to $R^4$, $R^{1'}$ to $R^{4'}$, and $R^6$ are as defined above; can be produced by the above-described method.

Specific examples of the diaryl sulfone compound of Formula (5) include 4,4'-di(3-hydroxypropylthio)diphenyl sulfone, 4,4'-di(2-hydroxyethylthio)diphenyl sulfone, 4,4'-di(2-hydroxypropiothio)diphenyl sulfone, and the like.

The resulting diaryl sulfone compound can be obtained, if necessary, by water-washing and liquid-liquid separation. The diaryl sulfone compound can also be isolated with high purity by recrystallization after distilling off the solvent.

Subsequently, the diaryl sulfone compound represented by Formula (5) is reacted with a halogenating agent.

Examples of halogenating agents that can be used include chlorine, thionyl chloride, hypochlorous acid, hypobromous acid, bromine, and the like. Thionyl chloride is preferable from economic and operational viewpoints.

The amount of halogenating agent used is preferably about 2 to 6 mol, more preferably about 2 to 3 mol, per mole of the diaryl sulfone compound represented by Formula (5).

The reaction of the diaryl sulfone compound of Formula (5) with a halogenating agent can be usually performed in an organic solvent. Examples of the organic solvent include polar solvents such as dimethylsulfoxide, N-methylpyrrolidone, and N,N-dimethylformamide (DMF); halogenated hydrocarbons such as methylene chloride, 1,2-dichloroethane, chlorobenzene, and o-dichlorobenzene; hydrocarbons such as n-hexane, n-heptane, cyclohexane, toluene, and xylene; and the like. DMF or toluene is preferable from an economic viewpoint.

The amount of solvent used is preferably about 10 to 5,000 parts by weight, more preferably about 100 to 1,000 parts by weight, relative to 100 parts by weight of the diaryl sulfone compound represented by Formula (5).

The reaction temperature is preferably about 30 to 120° C., and more preferably about 50 to 90° C. The reaction time is usually about 1 to 30 hours.

The diaryl sulfone compound represented by Formula (6):

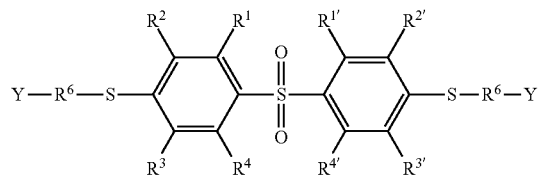

wherein $R^1$ to $R^4$, $R^{1'}$ to $R^{4'}$, and $R^6$ are as defined above, and Y is halogen;
can be produced by the above-described method.

Specific examples of the diaryl sulfone compound represented by Formula (6) include 4,4'-di(3-chloropropylthio) diphenyl sulfone, 4,4'-di(2-chloroethylthio)diphenyl sulfone, 4,4'-di(3-bromopropylthio)diphenyl sulfone, 4,4'-di(2-bromoethylthio)diphenyl sulfone, and the like.

The resulting diaryl sulfone compound of Formula (6) can be obtained, if necessary, by water-washing and liquid-liquid separation. The diaryl sulfone compound can also be isolated with high purity by recrystallization after distilling off the solvent.

Next, the diaryl sulfone compound represented by Formula (6) is reacted with a base to perform dehydrohalogenation reaction (HY elimination reaction).

Examples of the base used in this reaction include sodium hydroxide, potassium hydroxide, calcium hydroxide, lithium hydroxide, sodium carbonate, potassium carbonate, calcium carbonate, lithium carbonate, and the like. Sodium hydroxide, potassium hydroxide, calcium hydroxide, and the like are particularly preferable.

The amount of base used is preferably about 1 to 10 mol, more preferably about 1 to 4 mol, per mole of the diaryl sulfone compound represented by Formula (6).

The above-described reaction is usually carried out in a solvent. As the solvent, a polar solvent such as dimethylsulfoxide, N-methylpyrrolidone, N,N-dimethylformamide, or the like; a biphasic solvent consisting of the polar solvent and water; or the like can be used. N,N-dimethylformamide (DMF) is particularly preferable from an economic viewpoint.

The amount of solvent used is preferably about 10 to 5,000 parts by weight, more preferably about 100 to 1,000 parts by weight, relative to 100 parts by weight of the diaryl sulfone compound represented by Formula (6).

The reaction temperature is preferably about 30 to 120° C., and more preferably about 60 to 100° C. The reaction time is usually about 1 to 30 hours.

The diaryl sulfone compound represented by Formula (6) undergoes a dehydrohalogenation reaction (HY elimination reaction) by the above method, thereby producing the desired diaryl sulfone compound represented by Formula (1-2):

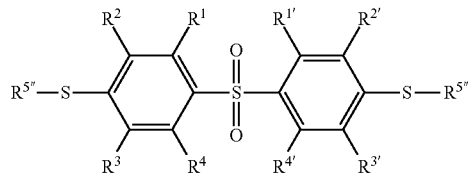

wherein $R^1$ to $R^4$ and $R^{1'}$ to $R^{4'}$ are the same or different, and each represents hydrogen, $C_{1-4}$ alkyl, or halogen; and $R^{5''}$ represents $C_{2-6}$ alkenyl.

The resulting diaryl sulfone compound can be obtained, if necessary, by water-washing and liquid-liquid separation. The diaryl sulfone compound can also be isolated with high purity by recrystallization after distilling off the solvent.

Specific examples of the diaryl sulfone compound produced by the above method include 4,4'-di(vinylthio)diphenyl sulfone, 4,4'-di(allylthio)diphenyl sulfone, 4,4'-di(isopropenylthio)diphenyl sulfone, and the like.

Advantageous Effects of Invention

According to the method of the present invention, the desired diaryl sulfone compound represented by Formula (1) can be obtained with a good yield with a relatively simple production process, using the 4,4'-dihalodiaryl sulfone compound represented by Formula (2), which is an inexpensive substance, as a starting material.

Of the diaryl sulfone compounds obtained by this method, the compound in which $R^5$ is alkenyl is a useful compound as a monomer that is used for producing synthetic resin for optical materials having a high refractive index and good transparency, and the compound can be effectively used as a raw material for optical materials, such as plastic lenses for glasses, Fresnel lenses, lenticular lenses, optical disk bases, and plastic optical fibers.

Further, the diaryl sulfone compound in which $R^5$ is alkyl or aromatic heterocyclic group is a substance having a high refractive index (1.64 or higher); and can be effectively used, for example, as an additive for imparting a high refractive index to organic optical materials.

DESCRIPTION OF EMBODIMENTS

The present invention is described in further detail below with reference to examples.

Example 1

Production of 4,4'-Di(allylthio)diphenyl Sulfone (First Method)

4,4'-Dichlorodiphenyl sulfone (14.4 g, 50 mmol), 2-propenethiol (7.8 g, 105 mmol), and N-methylpyrrolidone (100.0 g) were placed in a 500 ml-flask equipped with a stirrer, a thermometer, a condenser, and a gas inlet tube; sodium hydride (4.2 g, 105 mmol) was dividedly added thereto while maintaining the temperature of the solution at 10° C.; and the temperature of the solution was raised to 50° C. under stirring to perform reaction for 1 hour.

After the reaction was completed, the temperature of the solution was cooled to 10° C., and water (275 g) was added dropwise thereto. Subsequently, the reaction solution was filtered, thereby obtaining 4,4'-di(allylthio)diphenyl sulfone (10.9 g). The yield relative to 4,4'-dichlorodiphenyl sulfone was 60%.

$^1$H NMR; d 3.62 (dd, J=1.2 Hz, 6.4 Hz, 4H), 5.17 (dd, J=1.2 Hz, 6.4 Hz, 2H), 5.27 (dd, J=1.2 Hz, 16.8 Hz, 2H), 5.80-5.90 (m, 2H), 7.32 (d, J=8.8 Hz, 4H), 7.78 (d, J=8.4 Hz, 4H);

Elemental analysis (as $C_{18}H_{18}O_2S_3$);
Calculated: C, 59.63%; H, 5.00%; O: 8.83%; S: 26.53%.
Found: C, 59.65%; H, 5.00%; O: 8.80%; S: 26.54%.
Refractive index: 1.656

Example 2

Production of 4,4'-Di(vinylthio)diphenyl Sulfone (Second Method)

(i) Production Process of 4,4'-Di(2-hydroxyethylthio)diphenyl Sulfone 4,4'-Dichlorodiphenyl sulfone (14.4 g, 50 mmol), 2-hydroxyethanethiol (8.2 g, 105 mmol), and N-methylpyrrolidone (100.0 g) were placed in a 500 mL-flask equipped with a stirrer, a thermometer, a condenser, and a gas inlet tube, and sodium hydride (4.2 g, 105 mmol) was dividedly added thereto while maintaining the temperature of the solution at 10° C. The temperature of the solution was raised to 50° C. under stirring to perform reaction for 2 hours. After the reaction was completed, the temperature of the solution was cooled to 10° C., and water (200.0 g) was added dropwise thereto. Subsequently, extraction was performed using dichloromethane (100.0 g). The extracted oil layer was washed with water (100.0 g), and dichloromethane was distilled off, thereby obtaining 4,4'-di(2-hydroxyethylthio)diphenyl sulfone (16.7 g). The yield relative to 4,4'-dichlorodiphenyl sulfone was 90%.

(ii) Production Process of 4,4'-Di(2-chloroethylthio)diphenyl Sulfone 4,4'-Di(2-hydroxyethylthio)diphenyl sulfone (7.4 g, 20 mmol) and N,N-dimethylformamide (15.0 g) were placed in a 300 mL-flask equipped with a stirrer, a thermometer, a condenser, and a gas inlet tube, and the temperature was raised. While the temperature of the solution was maintained at 70° C., thionyl chloride (4.9 g, 41 mmol) was added dropwise thereto to perform reaction for 2 hours under stirring.

After the reaction was completed, the temperature of the solution was cooled to 25° C., and water (30.0 g) was added dropwise thereto. Then, 30% by weight aqueous solution of sodium hydroxide (9.8 g, 74 mmol) was added dropwise thereto. Subsequently, water (100.0 g) and dichloromethane (50.0 g) were added, and the oil layer was separated. Afterward, dichloromethane was distilled off, acetonitrile (50.0 g) was added dropwise, water (150.0 g) was added dropwise, and then filtration was performed, thereby obtaining 4,4'-di(2-chloroethylthio)diphenyl sulfone (7.3 g). The yield relative to 4,4'-di(2-hydroxyethylthio)diphenyl sulfone was 90%.

(iii) Production Process of 4,4'-Di(vinylthio)diphenyl Sulfone 4,4'-Di(2-chloroethylthio)diphenyl sulfone (2.0 g, 5 mmol) and N,N-dimethylformamide (6.0 g) were placed in a 50 mL-flask equipped with a stirrer, a thermometer, a condenser, and a gas inlet tube, and the temperature was raised. While maintaining the temperature of the solution at 80° C., 30% by weight aqueous solution of sodium hydroxide (2.3 g, 17 mmol) was added dropwise thereto to perform reaction for 3 hours under stirring. After the reaction was completed, the temperature of the solution was cooled to 25° C., water (30.0 g) was added dropwise, and then filtration was performed, thereby obtaining 4,4'-di(vinylthio)diphenyl sulfone (1.2 g). The yield relative to 4,4'-di(2-chloroethylthio)diphenyl sulfone was 70%.

$^1$H NMR: d 5.62 (dd, J=9.2 Hz, 16.4 Hz, 4H), 6.52 (dd, J=9.2 Hz, 16.4 Hz, 2H), 7.38 (d, J=8.8 Hz, 4H), 7.83 (d, J=8.4 Hz, 4H);

Elemental analysis (as $C_{16}H_4O_2S_3$);
Calculated: C, 57.45%; H, 4.22%; O: 9.57%; S: 28.76%.
Found: C, 57.40%; H, 4.18%; O: 9.63%; S: 28.79%.
Refractive index: 1.651

Example 3

Production of 4,4'-Di(methylthio)diphenyl Sulfone 4,4'-Dichlorodiphenyl sulfone (61.0 g, 212 mmol), toluene (75.0 g), and 50% by weight aqueous solution of tetra-n-butylammonium bromide (1.0 g) were placed in a 300 mL-flask equipped with a stirrer, a thermometer, a condenser, and a gas inlet tube, and the temperature was raised. While the temperature of the solution was maintained at 60° C., 32% by weight aqueous solution of sodium methanethiolate (97.5 g, 445 mmol) was added dropwise thereto to perform reaction for 5 hours under stirring.

After the reaction was completed, the temperature of the solution was cooled to 25° C., and filtration was performed, thereby obtaining 4,4'-di(methylthio)diphenyl sulfone.

Next, the obtained crude 4,4'-di(methylthio)diphenyl sulfone and acetonitrile (150.0 g) were placed in a 300 mL-flask equipped with a stirrer, a thermometer, a condenser, and a gas inlet tube, and dissolved by increasing the temperature of the solution to 80° C. After dissolution, the temperature of the solution was cooled to 10° C., and filtration was performed, thereby obtaining 4,4'-di(methylthio)diphenyl sulfone (62.5 g). The yield relative to 4,4'-dichlorodiphenyl sulfone was 95%.

$^1$H NMR d 2.48 (s, 6H), 7.27 (d, J=8.4 Hz, 4H), 7.79 (d, J=8.8 Hz, 4H);

Elemental analysis (as $C_{14}H_{14}O_2S_3$);
Calculated: C, 54.16%; H, 4.55%; O: 10.31%; S: 30.99%.
Found C, 54.19%; H, 4.61%; O: 10.27%; S: 30.94%.
Refractive index: 1.644

Example 4

Production of 4,4'-Di(2-benzothiazolylthio)diphenyl Sulfone 4,4'-Dichlorodiphenyl sulfone (14.4 g, 50 mmol), 2-benzothiazolethiol (17.6 g, 105 mmol), and N-methylpyrrolidone (100.0 g) were placed in a 500 mL-flask equipped with a stirrer, a thermometer, a condenser, and a gas inlet tube; sodium hydride (4.2 g, 105 mmol) was dividedly added thereto while maintaining the temperature of the solution at 10° C.; and the temperature of the solution was raised to 150° C. under stirring to perform reaction for 13 hours.

After the reaction was completed, the temperature of the solution was cooled to 10° C., and water (257 g) was added dropwise thereto. Subsequently, the reaction solution was filtered, thereby obtaining 4,4'-di(2-benzothiazolylthio)diphenyl sulfone (16.7 g). The yield relative to 4,4'-dichlorodiphenyl sulfone was 90%.

$^1$H NMR d 7.35-7.49 (m, 4H), 7.73-7.79 (m, 6H), 7.92-8.00 (m, 6H);

Elemental analysis (as $C_{26}H_{16}N_2O_2S_5$);
Calculated: C, 56.91%; H, 2.94%; N, 5.11%; O: 5.83%; S: 29.22%.
Found C, 56.87%; H, 2.91%; N, 5.14%; O: 5.88%; S: 29.21%.
Refractive index: 1.692

The invention claimed is:

1. A diaryl sulfone compound represented by Formula (1):

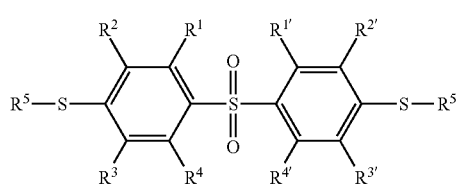

wherein $R^1$ to $R^4$ and $R^{1'}$ to $R^{4'}$ are the same or different, and each represents hydrogen, $C_{1-4}$ alkyl, or halogen; and $R^5$ represents vinyl, allyl, isopropenyl, 1-butenyl, 2-butenyl, 3-butenyl, isobutenyl, methyl, ethyl, n-propyl, isopropyl, or aromatic heterocyclic group, wherein the aromatic heterocyclic group is selected from the group consisting of thienyl, pyrrolyl, furyl, thiazolyl, isothiazolyl, imidazolyl, pyrazolyl, oxazolyl, pyridyl, pyrazinyl, pyrimidinyl, pyridazinyl, isooxazolyl, isoquinolyl, isoindolyl, indazolyl, indolyl, quinoxalinyl, quinolyl, benzothiazolyl, benzisothiazolyl, benzimidazolyl, and benzofuranyl.

2. The diaryl sulfone compound according to claim 1, wherein the aromatic heterocyclic group is an aromatic heterocyclic group having two or more different heteroatoms.

3. The diaryl sulfone compound according to claim 1, wherein $R^5$ is vinyl, allyl, methyl, benzothiazolyl, or benzisothiazolyl.

4. The diaryl sulfone compound according to claim 1, wherein $R^1$ to $R^4$ and $R^{1'}$ to $R^{4'}$ are all hydrogen, and $R^5$ is vinyl, allyl, methyl, benzothiazolyl, or benzisothiazolyl.

5. A method for producing a diaryl sulfone compound represented by Formula (1-1):

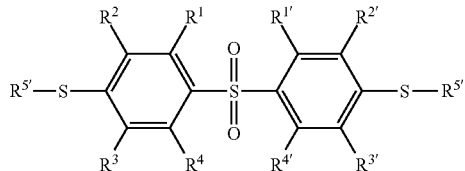

wherein $R^1$ to $R^4$ and $R^{1'}$ to $R^{4'}$ are the same or different, and each represents hydrogen, $C_{1-4}$ alkyl, or halogen, and $R^{5'}$ represents allyl, isopropenyl, 1-butenyl, 2-butenyl, 3-butenyl, isobutenyl, methyl, ethyl, n-propyl, isopropyl, or aromatic heterocyclic group wherein the aromatic heterocyclic group is selected from the group consisting of thienyl, pyrrolyl, furyl, thiazolyl, isothiazolyl, imidazolyl, pyrazolyl, oxazolyl, pyridyl, pyrazinyl, pyrimidinyl, pyridazinyl, isooxazolyl, isoquinolyl, isoindolyl, indazolyl, indolyl, quinoxalinyl, quinolyl, benzothiazolyl, benzisothiazolyl, benzimidazolyl, and benzofuranyl;

the method comprising reacting a 4,4'-dihaloarylsulfone compound represented by Formula (2):

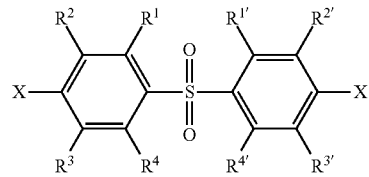

wherein $R^1$ to $R^4$ and $R^{1'}$ to $R^{4'}$ are as defined above, and X represents halogen;

with a thiol salt compound represented by Formula (3): $MSR^{5'}$, wherein M represents an alkali metal, and $R^{5'}$ is as defined above.

6. The method according to claim 5, wherein, in the 4,4'-dihaloarylsulfone compound represented by Formula (2), $R^1$ to $R^4$ and $R^{1'}$ to $R^{4'}$ are all hydrogen, and X is chlorine.

7. The method according to claim 5, wherein the thiol salt compound represented by Formula (3) is a compound selected from the group consisting of sodium-2-propenethiolate, potassium-3-butenethiolate, sodium methanethiolate, potassium-1-propanethiolate, sodium-2-propanethiolate, lithium-sec-butylthiolate, sodium-tert-butylthiolate, sodium-2-benzothiazolylthiolate, potassium-2-thiazolylthiolate, and sodium-3-isothiazolylthiolate.

8. The method according to claim 6, wherein the thiol salt compound represented by Formula (3) is a compound selected from the group consisting of sodium-2-propenethiolate, potassium-3-butenethiolate, sodium methanethiolate, potassium-1-propanethiolate, sodium-2-propanethiolate, lithium-sec-butylthiolate, sodium-tert-butylthiolate, sodium- 2-benzothiazolylthiolate, potassium-2-thiazolylthiolate, and sodium-3-isothiazolylthiolate.

9. The diaryl sulfone compound according to claim 4, wherein $R^5$ is vinyl, allyl, methyl, or benzothiazolyl.

* * * * *